US007175653B2

(12) United States Patent
Gaber

(10) Patent No.: US 7,175,653 B2
(45) Date of Patent: Feb. 13, 2007

(54) SELECTIVELY EXPANDABLE AND RELEASABLE STENT

(75) Inventor: Benny Gaber, Tirat Hacarmel (IL)

(73) Assignee: Xtent Medical Inc., Wilmington, DE (US)

(*) Notice: Subject to any disclaimer, the term of this patent is extended or adjusted under 35 U.S.C. 154(b) by 689 days.

(21) Appl. No.: 10/276,275

(22) PCT Filed: May 3, 2001

(86) PCT No.: PCT/IL01/00395

§ 371 (c)(1),
(2), (4) Date: Mar. 21, 2003

(87) PCT Pub. No.: WO01/87180

PCT Pub. Date: Nov. 22, 2001

(65) Prior Publication Data
US 2003/0208262 A1 Nov. 6, 2003

(30) Foreign Application Priority Data
May 17, 2000 (IL) .................................... 136213

(51) Int. Cl.
A61F 2/82 (2006.01)
(52) U.S. Cl. ..................................... 623/1.15; 623/1.11

(58) Field of Classification Search ............... 623/1.11, 623/1.12, 1.15; 606/198
See application file for complete search history.

(56) References Cited

U.S. PATENT DOCUMENTS 4,954,126 A * 9/1990 Wallsten ...................... 600/36
5,411,549 A 5/1995 Peters

FOREIGN PATENT DOCUMENTS

EP 0 737 453 10/1996
WO WO 99/13800 3/1999

* cited by examiner

Primary Examiner—Michael Thaler
(74) Attorney, Agent, or Firm—Ladas and Parry LLP

(57) ABSTRACT

A stent including a plurality of loops, each of the loops includes an arcuately formed wire with a first end and a second end, the first end being attached to an inner elongate member and the second end being attached to an outer elongate member, the inner and the outer elongate members being arranged to slide with respect to each other along a common longitudinal axis, wherein sliding of the inner and the outer elongate members with respect to each other changes a cross-sectional area of each of the loops, characterized in that the inner and outer elongate members are attached to inner and outer coupler tubes, and are selectively releasable from the inner and outer coupler tubes, the inner coupler tube being nested inside the outer coupler tube.

18 Claims, 5 Drawing Sheets

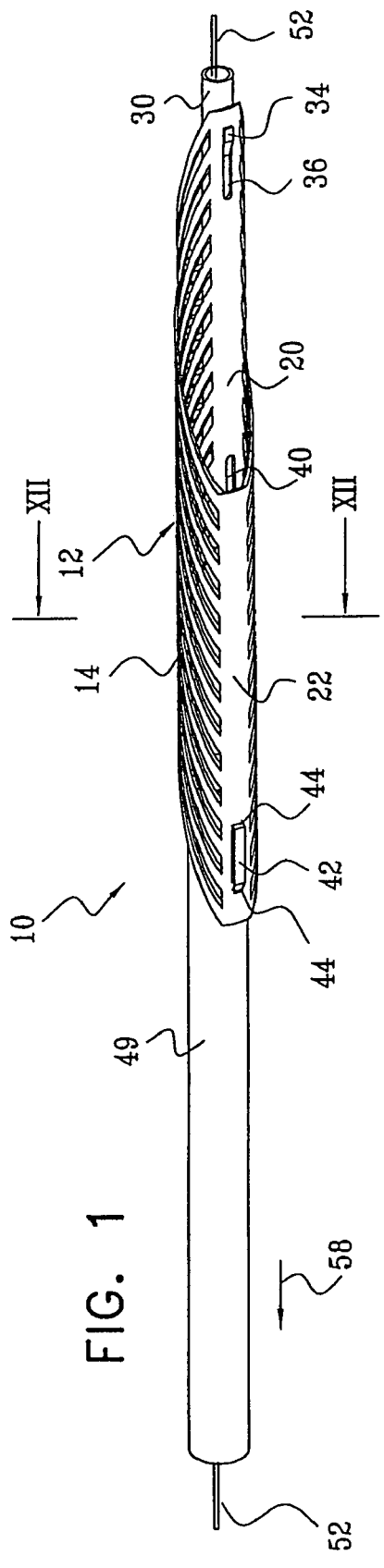
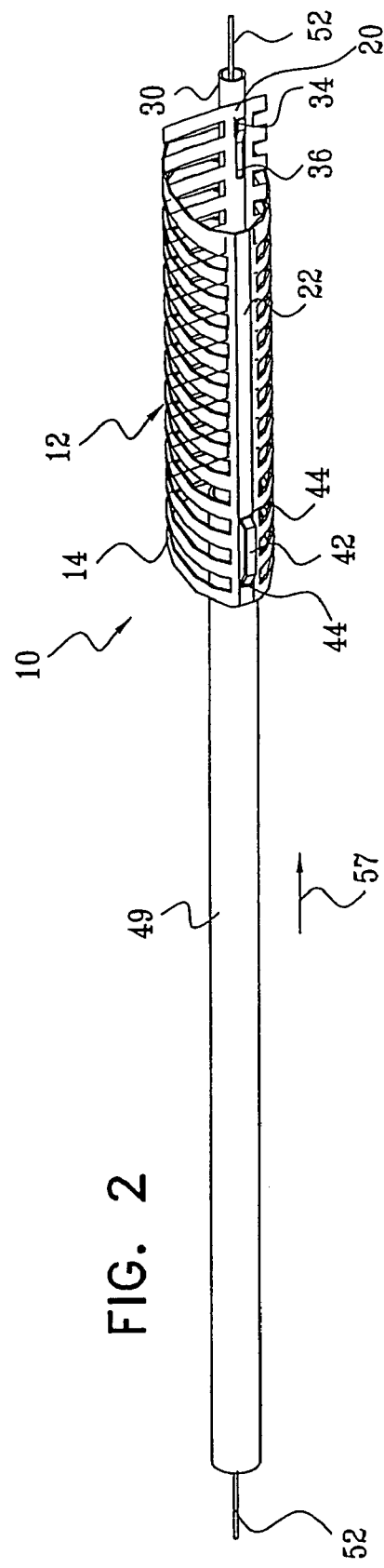
FIG. 1
FIG. 2

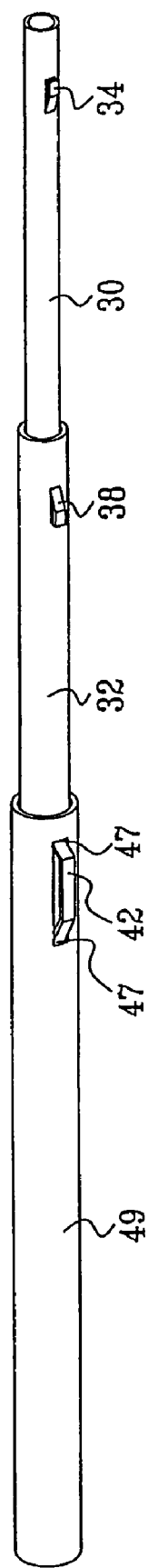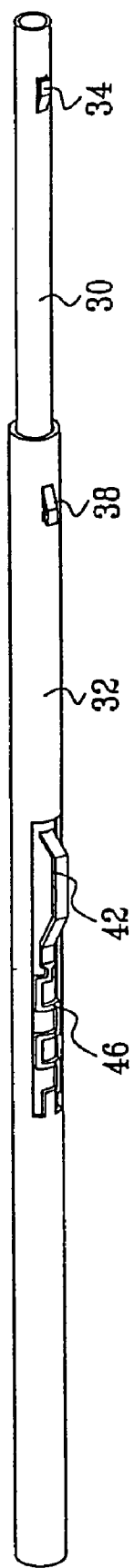
FIG. 5A
FIG. 5B

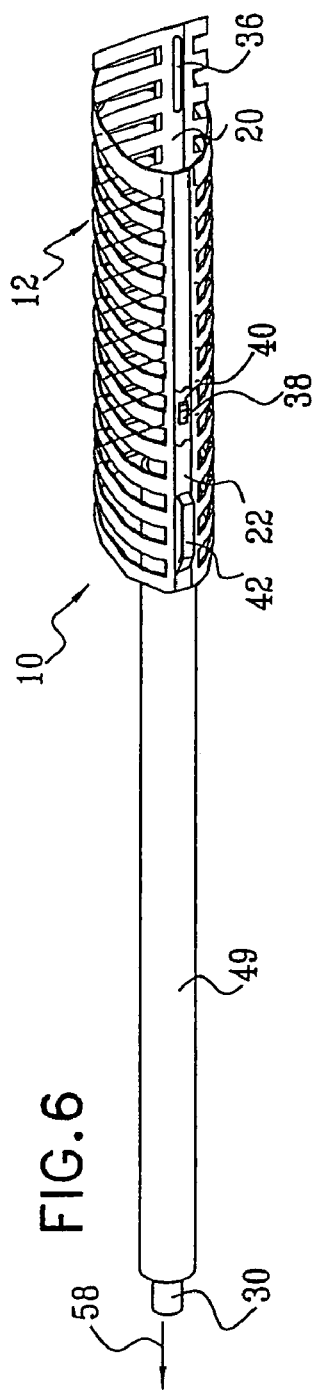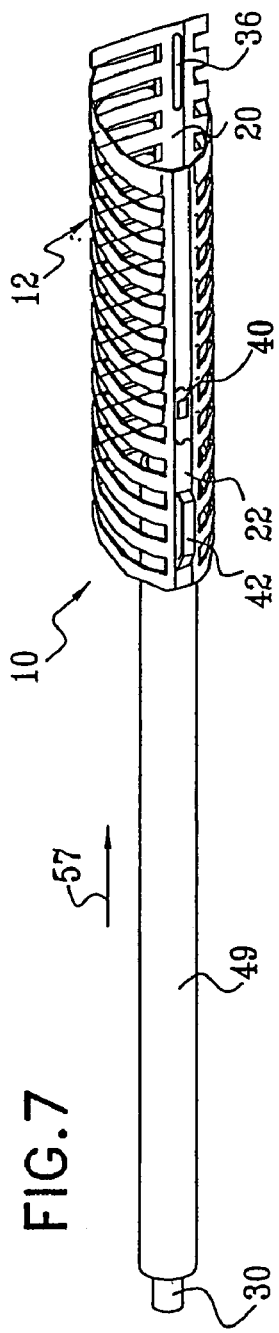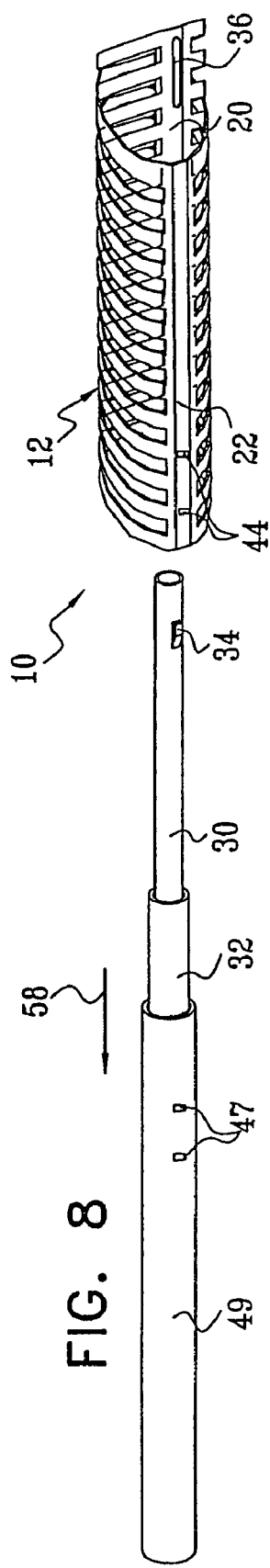

SELECTIVELY EXPANDABLE AND RELEASABLE STENT

FIELD OF THE INVENTION

The present invention relates generally to a stent with a selectively changeable cross-sectional area which is easily inserted into and removed from a body vessel, and which is selectively expandable and releasable.

BACKGROUND OF THE INVENTION

Stents are well known tubular support structures inserted into body vessels, ducts, lumens and the like, in various medical procedures. For example, stents may be inserted in strictures in the common bile duct, blood vessels, urethra and other organs. Stents are generally mounted on a delivery catheter which is inserted over a thin guidewire. The catheter is introduced into the particular vessel, and the stent is released from the catheter and fixed in a chosen location in the vessel by expanding a balloon upon which the stent is mounted in a closed position. A disadvantage of such prior arts is that as long as the balloon is expanded, blood cannot flow therepast. Both the balloon and the stent have only two positions, either fully open or fully closed. There is no possibility of adjusting the diameter of the stent. After having installed the stent, there is no possibility of adjusting the stent position in the vessel.

Another disadvantage is that prior art stents cannot be installed in very constricted vessels without first enlarging the constricted vessel. This is usually accomplished by first introducing a deflated balloon to the constricted area, expanding the balloon in an effort to expand the constriction, removing the balloon and finally inserting the stent in place. This balloon procedure can lead to endothelial ablation. Moreover, as mentioned before, while the balloon is expanded, there is no blood flow therepast.

Recently expandable stents have been developed. A particularly relevant expandable stent is described in published PCT patent application WO 99/13800, assigned to the present assignee/applicant, the disclosure of which is incorporated herein by reference. The stent preferably includes a plurality of loops, each of the loops including an arcuately formed wire with a first end and a second end. The first end is preferably attached to a first elongate member and the second end is preferably attached to a second elongate member. The inner and outer elongate members are preferably arranged to slide with respect to each other along a common longitudinal axis, wherein the loops are arranged in a row and spaced from each other along the longitudinal axis. Sliding of the inner and outer elongate members with respect to each other changes a cross-sectional area of each of the loops.

The WO 99/13800 stent has many advantages. The stent is not only easily insertable, but also easily removable. Since the stent is hollow and there is no balloon, blood continuously can flow through the stent at all times during and after installation. This, plus the fact that the stent can be expanded and contracted at will during installation, means that the stent can replace the balloon in certain angioplasty procedures. The stent can be expanded to a wide range of diameter sizes, and the diameter can be adjusted. Even after having installed the stent, the stent position in the vessel can be adjusted. The absence of the balloon eliminates the problem of endothelial ablation.

SUMMARY OF THE INVENTION

The present invention seeks to provide further improvements in the WO 99/13800 stent. The stent is selectively expandable/contractible throughout a range of cross-sectional areas, and is easily insertable and removable.

There is thus provided in accordance with a preferred embodiment of the present invention a stent including a plurality of loops, each of the loops including an arcuately formed wire with a first end and a second end, the first end being attached to an inner elongate member and the second end being attached to an outer elongate member, the inner and the outer elongate members being arranged to slide with respect to each other along a common longitudinal axis, wherein sliding of the inner and the outer elongate members with respect to each other changes a cross-sectional area of each of the loops, characterized in that the inner and outer elongate members are attached to inner and outer coupler tubes, and are selectively releasable from the inner and outer coupler tubes, the inner coupler tube being nested inside the outer coupler tube. The loops preferably cross over each other in a braided arrangement.

In accordance with a preferred embodiment of the present invention the inner coupler tube is formed with a bendable tab which is inserted through a first aperture formed in the inner elongate member.

Further in accordance with a preferred embodiment of the present invention the outer coupler tube is formed with a bendable tab which is inserted through a second aperture formed in the inner elongate member.

Still further in accordance with a preferred embodiment of the present invention the outer coupler tube is formed with a tongue which is inserted through an aperture formed in the outer elongate member.

Additionally in accordance with a preferred embodiment of the present invention the outer coupler tube includes an expandable, resilient portion from which extends the tongue.

In accordance with a preferred embodiment of the present invention the outer coupler tube is nested in a flexible manipulator tube. Preferably the tongue passes through a pair of apertures formed in the manipulator tube.

Further in accordance with a preferred embodiment of the present invention the inner and outer coupler tubes are constructed of a flexible plastic material. The flexible plastic material may include embedded reinforced wires. Alternatively, the inner and outer coupler tubes may be constructed of a flexible metal. Still alternatively, the inner and outer coupler tubes may be constructed with multiple openings formed on circumferences thereof.

In accordance with a preferred embodiment of the present invention the stent is slid over a guide wire. Alternatively, the stent may be attached to the guide wire.

Further in accordance with a preferred embodiment of the present invention pulling the inner coupler tube generally proximally pulls the tab of the inner coupler tube out of the first aperture, thereby releasing the inner coupler tube from the inner elongate member.

Still further in accordance with a preferred embodiment of the present invention pushing the manipulator tube generally distally pushes the outer coupler tube generally distally, and pushes the tab of the outer coupler tube out of the second aperture, thereby releasing the outer coupler tube from the inner elongate member.

In accordance with a preferred embodiment of the present invention pulling the inner and outer coupler tubes generally proximally releases the tongue from the apertures of the outer elongate member, thereby allowing proximally-directed removal of the inner and outer coupler tubes and the manipulator tube.

BRIEF DESCRIPTION OF THE DRAWINGS

The present invention will be understood and appreciated more fully from the following detailed description, taken in conjunction with the drawings in which:

FIGS. 1 and 2 are simplified pictorial illustrations of a stent constructed and operative in accordance with a preferred embodiment of the present invention, and comprising a plurality of loops of wire attached to a pair of elongate members, in respective contracted and expanded positions;

FIG. 5A is a simplified pictorial illustration showing the nesting of an inner coupler tube in an outer coupler tube;

FIG. 5B is a simplified pictorial illustration showing the nesting of the inner coupler tube in the outer coupler tube;

FIG. 6 is a simplified pictorial illustration of detaching the inner coupler tube from the inner elongate member by moving the inner coupler tube proximally;

FIG. 7 is a simplified pictorial illustration of detaching the outer coupler tube from the inner elongate member by moving the outer coupler tube distally;

FIG. 8 is a simplified pictorial illustration of detaching the outer coupler tube from the outer elongate member by moving the inner and outer coupler tubes proximally, and completely removing both coupler tubes and manipulator tube from the stent of FIG. 1 by moving all tubes proximally;

DETAILED DESCRIPTION OF A PREFERRED EMBODIMENT

Figure 3:
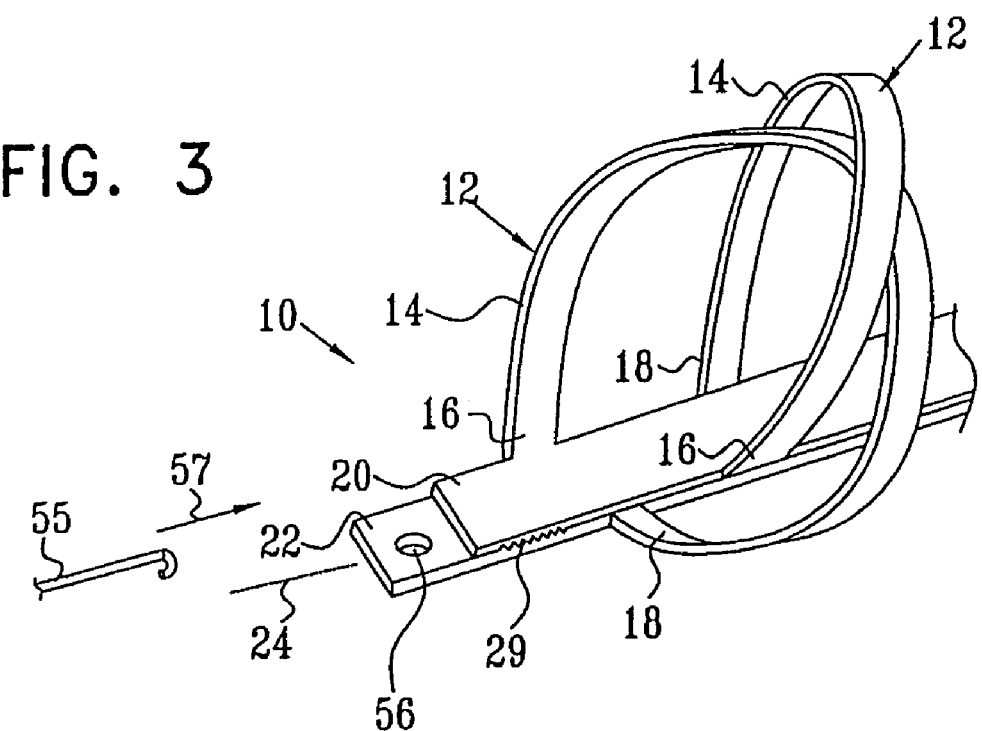
FIG. 3 is a simplified enlarged illustrations of the stent of FIG. 1, in respective expanded and contracted positions.

Reference is now made to FIGS. 1–3 which illustrate a stent 10 constructed and operative in accordance with a preferred embodiment of the present invention.

Stent 10 includes a plurality of loops 12, each loop 12 constructed of an arcuately formed wire 14 with a first end 16 and a second end 18 (FIG. 3). It is noted that throughout the specification and claims the term wire encompasses any slender element such as wire, rod, bar, cable, or the like, having any cross-sectional shape such as flat, rectangular or round. Wire 14 is typically made of any medically safe material and may be flexible if desired. For example, wire 14 may be made of a resilient material, such as heat-treated nitinol, wherein after inserting stent 10 in a lumen (not shown) and expanding stent 10 to its expanded position (FIG. 2), wires 14 tend to spring outwards against the inner walls of the lumen. This helps to anchor stent 10 in place and prevent migration of stent 10 inside the lumen.

First end 16 preferably extends from an inner elongate member 20 and second end 18 preferably extends from an outer elongate member 22. Inner and outer elongate members 20 and 22 are preferably arranged to slide with respect to each other along a common longitudinal axis 24.

In a preferred embodiment of the present invention, loops 12 cross over each other in a braided arrangement, as seen in FIGS. 1–3. Alternatively, loops 12 may be arranged in a row and spaced from each other along axis 24, as described in the stent of WO 99/13800.

Figure 9:
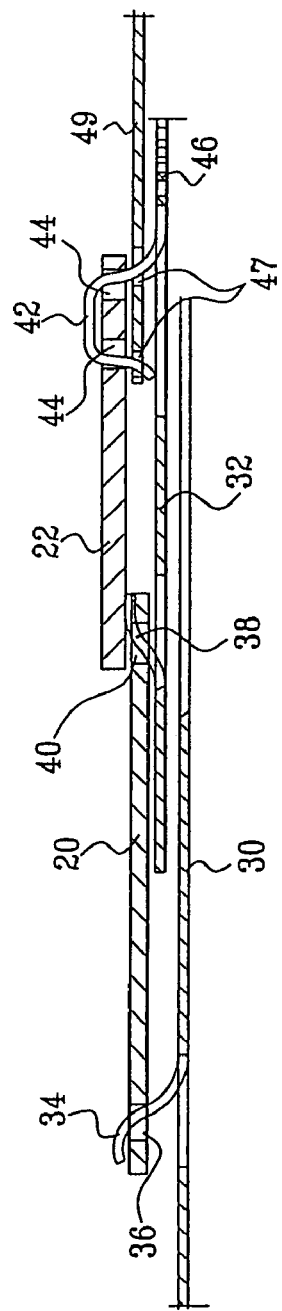
FIG. 9 is a simplified sectional illustration of the stent of FIG. 1.
Figure 11:
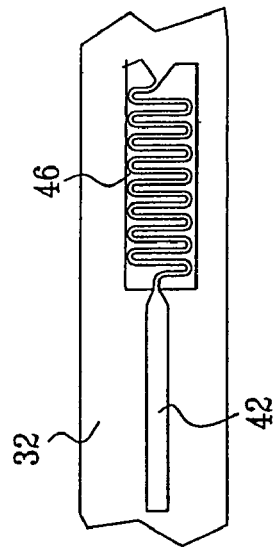
FIG. 11 is a simplified pictorial illustration of an expandable, resilient portion of the outer coupler tube, constructed and operative in accordance with a preferred embodiment of the present invention.
Figure 10:
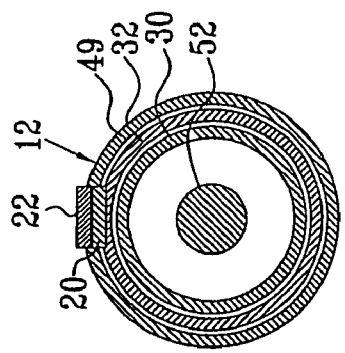
FIG. 10 is a simplified pictorial illustration of a bendable tab of the inner coupler tube, constructed and operative in accordance with a preferred embodiment of the present invention.

Inner and outer elongate members 20 and 22 are preferably attached to inner and outer coupler tubes 30 and 32 (FIGS. 5A and 5B). Referring additionally to FIGS. 9–11, it is seen that inner coupler tube 30 is preferably formed with one or more bendable tabs 34 that are bent and inserted through one or more apertures 36 formed in inner elongate member 20. The tabs 34 may be formed by making a cut 35 in inner coupler tube 30 as shown in FIG. 10. Outer coupler tube 32 is preferably formed with one or more bendable tabs 38 that are bent and inserted through one or more apertures 40 formed in inner elongate member 20. Outer coupler tube 32 is also preferably formed with a tongue 42 that is bendable and insertable through one or more pairs of apertures 44 formed in outer elongate member 22. Outer coupler tube 32 preferably includes an expandable, resilient portion 46 extending in a serpentine or accordion-like manner from which extends tongue 42.

Tongue 42 preferably also passes through a pair of apertures 47 formed in a manipulator tube 49, thereby attaching outer elongate member 22 and outer coupler tube 32 to manipulator tube 49. Inner coupler tube 30 is nested in outer coupler tube 32, which in turn is nested in manipulator tube 49, as seen in FIGS. 5A and 5B.

Figure 4:
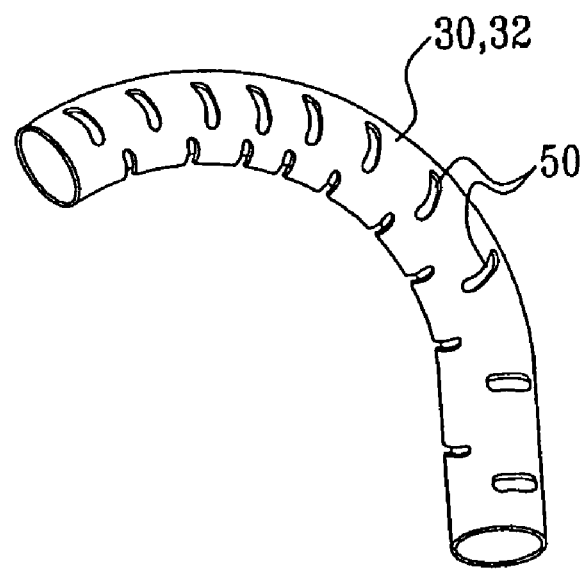
FIG. 4 is a simplified pictorial illustration of a slender, flexible coupler tube, on which the stent of FIG. 1 is detachably mounted.

Manipulator tube 49 is a long, flexible tube which extends over a guide wire 52 outwards of the patient to a doctor or other practitioner, and is used to expand or contract stent 10, as described hereinbelow. Inner and outer coupler tubes 30 and 32 also extend over guide wire 52 outwards of the patient, inside manipulator tube 49. Inner and outer coupler tubes 30 and 32 may be constructed of a flexible plastic material, with or without reinforced wires embedded in their walls, as is known in the art. Alternatively, inner and outer coupler tubes 30 and 32 may be constructed of a flexible metal, such as nitinol. As another alternative, shown in FIG. 4, inner and outer coupler tubes 30 and 32 may be constructed with multiple openings 50 formed on circumferences thereof, arranged in rows and columns, for example, or any other regular or irregular arrangement.

Inner and outer elongate members 20 and 22 are preferably selectively fixable with respect to each other along a range of positions along axis 24. Friction between inner and outer elongate members 20 and 22 is preferably sufficient to maintain the members fixed at any selected position. In addition, as mentioned above, wires 14 tend to spring outwards against the inner walls of the lumen, which also helps to anchor stent 10 in place. Optionally, inner and outer elongate members 20 and 22 may be provided with teeth 29 along axis 24 (FIG. 3). Teeth 29 may be selectively and fixably meshed with each other along a range of positions along axis 24. This is just one example of structure for selectively fixing inner and outer elongate members 20 and 22 with respect to each other, and it is appreciated that many other devices may be employed for this purpose within the scope of the invention.

Stent 10 is preferably introduced into a lumen (e.g., blood vessel) of a patient (not shown) by sliding inner and outer coupler tubes 30 and 32 and manipulator tube 49, with loops 12 and inner and outer elongate members 20 and 22 attached thereto, over guide wire 52, as seen in FIG. 1. Stent 10 is then moved in the contracted position of FIG. 1 to the place of interest (e.g., a lesion). Pushing manipulator tube 49 distally in the direction of an arrow 57, while inner and outer coupler tubes 30 and 32 are held stationary, expands loops 12 of stent 10 to the expanded position shown in FIG. 2. As mentioned above, loops 12 can be set at any desired diameter, and can be adjusted during installation at will by simply pushing manipulator tube 49 distally to expand loops 12, and pulling manipulator tube 49 proximally, in the direction of an arrow 58 opposite to the direction of arrow 57, to contract the loops 12. The position of stent 10 can be adjusted easily by contracting the loops 12, moving stent 10 to the new position, and re-expanding loops 12. Because stent 10 is hollow and blood can flow therethrough at all times, and since stent 10 can be expanded and contracted at will during installation, stent 10 can replace a balloon in certain angioplasty procedures.

Figure 12:
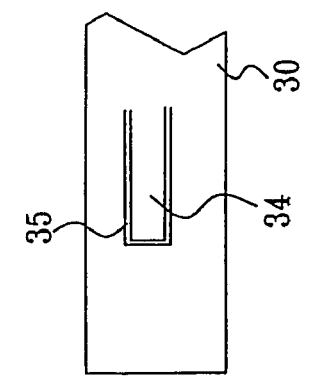
FIG. 12 is a simplified cross-sectional illustration of the stent of FIG. 1.

Reference is now made to FIG. 12, which is a cross-sectional view of the stent 10 taken along lines XII—XII in FIG. 1. FIG. 12 shows the location of the tubes 49, 32 and 30, and the elongate members 20 and 22, relative to the guide wire 52.

If it is required to detach stent 10 from coupler tubes 30 and 32, and manipulator tube 49, such as when it is desired to leave stent 10 in the lumen, then the following procedure is followed, described with reference to FIGS. 6–8.

In FIG. 6, inner coupler tube 30 is pulled slightly proximally (arrow 58), which pulls tab 34 out of aperture 36, thereby releasing inner coupler tube 30 from inner elongate member 20. Once released from aperture 36, tab 34 preferably tends to spring radially inwards.

In FIG. 7, manipulator tube 49 is pushed distally (arrow 57), which pushes tab 38 out of aperture 40, thereby releasing outer coupler tube 32 from inner elongate member 20. It is noted that the movement of manipulator tube 49 does not release the connection between manipulator tube 49 and outer coupler tube 32, on account of the resilient portion 46 of tongue 42 which allows for the linear movement of manipulator tube 49 without disturbing the connection to outer coupler tube 32. Outer coupler tube 32 thus remains attached to outer elongate member 22.

In FIG. 8, inner and outer coupler tubes 30 and 32 are pulled generally proximally (arrow 58) with respect to manipulator tube 49, which releases tongue 42 from apertures 44. Inner and outer coupler tubes 30 and 32, and manipulator tube 49, can now be removed completely from the patient (not shown) by pulling them out proximally. This completes detachment of stent 10 in the lumen of the patient.

Even after stent 10 has been installed in the patient, the loop diameter can be reduced and stent 10 can be removed from the lumen and patient. This is easily accomplished by introducing a hooked-end wire 55 (seen in FIG. 3) in the lumen to the area of the stent 10 and connecting the hooked end of wire 55 to a hole 56 formed in outer elongate member 22, for example. Wire 55 can then be pulled generally proximally, which reduces the diameter of loops 12 and permits removal of stent 10.

It is noted that instead of introducing stent 10 over the guide wire 52, alternatively, stent 10 can be included on the guide wire 52 itself.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A stent comprising:
   a selectably and variably expandable stent assembly including:
   first and second mutually axially displaceable elongate elements, each having first and second elongate edges and a plurality of loops each joined at an end thereof to an edge of said first elongate element and at an opposite end thereof to an edge of said second elongate element,
   said plurality of loops including at least one pair of mutually crossing loops including:
   a first loop joined at a right end thereof directly to a first edge of of said first elongate element and at a left end thereof directly to a second edge of said second elongate element; and
   a second loop joined at a right end thereof directly to a first edge of said second elongate element and at a left end thereof directly to a second edge of said first elongate element.

2. A stent according to claim 1 and wherein:
   each of said plurality of loops comprises an arcuately formed wire with a first end and a second end, said first end being attached to said first elongate element and said second end being attached to said second elongate element, said first and said second elongate elements being arranged to slide with respect to each other along a common longitudinal axis, wherein sliding of said first and said second elongate elements with respect to each other changes a cross-sectional area of each of said plurality of loops; and
   said stent also comprising a stent cross-section controller including first and second at least partially mutually nested displacing elements which are removably attachable to said first and second mutually axially displaceable elongate elements for selectable mutual displacement thereof, said cross-section controller comprising inner and outer coupler tubes, said inner coupler tube being nested inside said outer coupler tube.

3. The stent according to claim 2 wherein said inner coupler tube is formed with a bendable tab which is inserted through an aperture formed in said first elongate element.

4. The stent according to claim 2 wherein said outer coupler tube is formed with a bendable tab which is inserted through an aperture formed in said first elongate element.

5. The stent according to claim 2 wherein said outer coupler tube is formed with a tongue which is inserted through an aperture formed in said second elongate element.

6. The stent according to claim 5 wherein said outer coupler tube comprises an expandable, resilient portion from which extends said tongue.

7. The stent according to claim 6 wherein said outer coupler tube is nested in a flexible manipulator tube.

8. The stent according to claim 7 wherein said tongue passes through a pair of apertures formed in said manipulator tube.

9. The stent according to claim 7 wherein pulling said inner coupler tube generally proximally pulls said tab of said inner coupler tube out of said aperture, thereby releasing said inner coupler tube from said first elongate element.

10. The stent according to claim 9 wherein pushing said manipulator tube generally distally pushes said outer coupler tube generally distally, and pushes said tab of said outer coupler tube out of said aperture, thereby releasing said outer coupler tube from said first elongate element.

11. The stent according to claim 10 wherein pulling said inner and outer coupler tubes generally proximally releases said tongue from said aperture of said second elongate element, thereby allowing proximally-directed removal of said inner and outer coupler tubes and said manipulator tube.

12. The stent according to claim 2 wherein said inner and outer coupler tubes are constructed of a flexible plastic material.

13. The stent according to claim 12 wherein said flexible plastic material includes embedded reinforced wires.

14. The stent according to claim 2 wherein said inner and outer coupler tubes are constructed of a flexible metal.

15. The stent according to claim 2 wherein said inner and outer coupler tubes are constructed with multiple openings formed on circumferences thereof.

16. The stent according to claim 2 and further comprising a guide wire over which said stent is slid.

17. The stent according to claim 2 and further comprising a guide wire to which said stent is attached.

18. The stent according to claim 2 wherein said loops cross over each other in a braided arrangement.

* * * * *